United States Patent [19]

Chester et al.

[11] 4,377,721

[45] Mar. 22, 1983

[54] ALKYLATION OF ISOPARAFFINS WITH OLEFINS

[75] Inventors: Arthur W. Chester; Yung-Feng Chu, both of Cherry Hill, N.J.

[73] Assignee: Mobil Oil Corporation, New York, N.Y.

[21] Appl. No.: 276,227

[22] Filed: Jun. 22, 1981

[51] Int. Cl.$^3$ ............................................... C07C 2/58
[52] U.S. Cl. ................................... 585/722; 585/331; 585/716
[58] Field of Search ............... 585/722, 314, 315, 316, 585/331, 716, 717, 715, 719, 726, 727

[56] References Cited

U.S. PATENT DOCUMENTS

| | | | |
|---|---|---|---|
| 3,541,001 | 11/1970 | Hirschler | 585/722 |
| 3,655,813 | 4/1972 | Kirsch et al. | 585/722 |
| 3,840,613 | 10/1974 | Eberly et al. | 585/722 |
| 3,972,983 | 8/1976 | Ciric | 423/328 |
| 4,021,331 | 5/1977 | Ciric | 208/111 |
| 4,300,015 | 11/1981 | Kirsch et al. | 585/722 |

*Primary Examiner*—Delbert E. Gantz
*Assistant Examiner*—A. Pal
*Attorney, Agent, or Firm*—Charles A. Huggett; Michael G. Gilman; Dennis P. Santini

[57] ABSTRACT

An improved process for alkylation of isoparaffins with olefins to yield a product which includes a high proportion of highly branched alkylates for blending into gasolines. The improved process comprises contacting the isoparaffins and olefins with a catalyst comprising ZSM-20, preferably a HZSM-20 zeolite or a rare-earth cation exchanged ZSM-20 zeolite.

15 Claims, No Drawings

ALKYLATION OF ISOPARAFFINS WITH OLEFINS

BACKGROUND OF THE INVENTION

Alkylation is the addition of an alkyl group to an organic molecule. In petroleum chemistry the process finds attractive utility in the reaction of an isoparaffin with an olefin molecule to yield an isoparaffin of higher molecular weight. Industrially, the concept depends on the reaction of a $C_2$–$C_5$ olefin with isobutane in the presence of an acidic catalyst, producing the so-called alkylate. This is a very valuable ingredient in the manufacture of premium gasolines because of its high octane rating and good response to tetraethyl lead.

The catalysts employed in the industry are hydrofluoric acid or sulfuric acid carried out under controlled temperature conditions. Low temperatures are required in the sulfuric acid process to minimize the side reaction of olefin polymerization. The acid strength has to be maintained at 98–100 percent by the addition of fresh acid and the continuous withdrawal of spent acid.

The hydrofluoric acid process is less temperature-sensitive and the acid is easily recovered and purified. Any traces of water in the feedstock, however, have to be eliminated owing to the extreme corrosivity of hydrofluoric acid/water solutions.

These process materials and conditions are expensive and troublesome with problems such as maintaining an acid/hydrocarbon emulsion, careful temperature control with refrigeration, product separation and waste problems. Zeolites have been used, e.g. U.S. Pat. No. 3,251,902, to eliminate these problems with varying degrees of success. The catalysts found useful are rare-earth metal cation exchanged faujasite Y type zeolites (REHY). They appear to age rapidly and cannot perform effectively at high olefin space velocities.

SUMMARY OF THE INVENTION

This invention relates to an improved process of reacting an isoparaffin with olefin molecules in the presence of a catalyst comprising a ZSM-20 zeolite to yield alkylate. The isoparaffins preferred contain from 4 to 7 carbon atoms and the preferred olefins contain from 2 to 7 carbon atoms. A particularly preferred isoparaffin is isobutane and a particularly preferred olefin is 1-butene, with or without isomers. Other isoparaffins include isopentane, ethylisobutane and dimethylisopentane, etc. Other olefins include ethylene, propylene, pentene, hexene, heptene, etc. ZSM-20 type zeolites have not been demonstrated previously to be active and selective for isoparaffin alkylation with olefins.

It has now been found that under similar conditions, rare-earth cation exchanged ZSM-20 zeolites give higher liquid yield and better quality products than REHY. This is because they are more active and selective than REHY. The catalyst of the present invention can be further improved by the introduction of other metal cations, such as $Ca^{+2}$. Furthermore, it may be steamed and/or sulfided to improve its stability and/or activity.

As a result of the curtailment of octane improving additives, e.g. tetraethyl lead, not only the production of unleaded gasoline has increased, but also the octane number specification of all grades is seen to increase. Isoparaffin-olefin alkylation is a key route to produce highly branched alkylates for blending into gasolines. However, as indicated above, conventional alkylation processes suffer from many difficulties and large pore zeolites, such as, ZSM-4 and ZSM-12 do not have high alkylation activity. The pores of ZSM-5 are too small for alkylation. It now has been found that the use of the solid catalyst ZSM-20 will eliminate most of the problems.

DESCRIPTION OF SPECIFIC EMBODIMENTS

The catalyst composition useful in this invention comprises synthetic crystalline aluminosilicate designated ZSM-20, a detailed description of which is found in U.S. Pat. Nos. 3,972,983 and 4,021,331.

The ZSM-20 composition has a characteristic X-ray diffraction pattern, the values of which are set forth in Table 1 hereinafter. The ZSM-20 composition can also be identified, in terms of mole ratios of oxides in the anhydrous state, as follows:

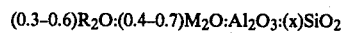

$$(0.3-0.6)R_2O:(0.4-0.7)M_2O:Al_2O_3:(x)SiO_2$$

wherein R is a tetraethylammonium cation, M is an alkali metal cation and x is at least 7.

In the as synthesized form, the zeolite has a formula in terms of mole ratios of oxides and in the anhydrous state, as follows:

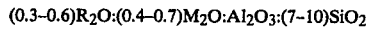

$$(0.3-0.6)R_2O:(0.4-0.7)M_2O:Al_2O_3:(7-10)SiO_2$$

wherein R is a tetraethylammonium cation and M is an alkali metal cation especially sodium.

Also, the zeolite ZSM-20 crystal structure is comprised of relatively uniform rigid three-dimensional pore network characterized by uniform pores of between 6 and 8 Angstrom units in diameter.

The original cations of the as synthesized ZSM-20 can be replaced in accordance with techniques well known in the art, at least in part, by ion exchange with other cations. Preferred replacing cations include metal ions, ammonium ions, hydrogen ions and mixtures thereof. Particularly preferred cations are those which render the zeolite catalytically-active, especially for the present process. These include hydrogen, hydrogen precursors (e.g. ammonium ions) and rare earth metals.

The synthetic ZSM-20 zeolite possesses a definite distinguishing hexagonal crystalline structure whose X-ray diffraction pattern shows substantially the significant lines set forth in Table 1.

TABLE 1

| d (A) | Relative Intensities |
|---|---|
| 14.90 ± 0.3 | VS |
| 14.21 ± 0.3 | VS |
| 8.67 ± 0.20 | M |
| 8.19 ± 0.15 | W |
| 7.44 ± 0.15 | M |
| 5.66 ± 0.10 | S |
| 5.34 ± 0.10 | W |
| 5.17 ± 0.10 | W |
| 5.00 ± 0.10 | W |
| 4.87 ± 0.10 | W |
| 4.74 ± 0.10 | W |
| 4.33 ± 0.09 | M |
| 3.98 ± 0.08 | W |
| 3.83 ± 0.08 | W |
| 3.76 ± 0.08 | M |
| 3.66 ± 0.07 | S |
| 3.60 ± 0.07 | W |
| 3.55 ± 0.07 | W |
| 3.45 ± 0.07 | W |
| 3.33 ± 0.07 | W |
| 3.29 ± 0.07 | M |

TABLE 1-continued

| d (A) | Relative Intensities |
|---|---|
| 3.20 ± 0.06 | W |
| 2.90 ± 0.06 | M |
| 2.87 ± 0.06 | W |
| 2.84 ± 0.06 | M |
| 2.79 ± 0.06 | W |
| 2.75 ± 0.06 | W |
| 2.70 ± 0.05 | W |
| 2.61 ± 0.05 | M |
| 2.41 ± 0.05 | W |
| 2.37 ± 0.05 | W |
| 2.17 ± 0.04 | W |
| 2.14 ± 0.04 | W |
| 2.09 ± 0.04 | W |
| 2.05 ± 0.04 | W |

These values were determined by standard techniques. The radiation was the K-alpha doublet of copper, and a scintillation counter spectrometer with a strip chart pen recorder was used. The peak heights I, and the position as a function of 2 times theta, where theta is the Bragg angle, were read from the spectrometer chart. From these, the relative intensities, 100 I/Io. where Io is the intensity of the strongest line or peak, and d (obs.), the interplanar spacing in Angstroms (A), corresponding to the recorded lines, were calculated. In Table I, relative intensities are listed according to the following symbol definitions: VS=very strong, S=strong, M=medium and W=weak. It should be understood that this X-ray diffraction pattern is characteristic of all the species of ZSM-20 compositions. Ion exchange of the sodium ion with cations reveals substantially the same pattern with some minor shifts in interplanar spacing and variation in relative intensity. Other minor variations can occur depending on the silicon to aluminum ratio of the particular sample, as well as if it has previously been subjected to thermal treatment.

Synthetic ZSM-20, when employed in the instant process, should be dehydrated at least partially. This can be done by heating it to a temperature in the range of 200° C. to 600° C. in an inert atmosphere, such as air, nitrogen, etc. and at atmospheric or subatmospheric pressures for between about 1 and 48 hours. Dehydration can also be performed at lower temperature merely by placing the catalyst in a vacuum, but a longer time is required to obtain a sufficient amount of dehydration.

Zeolite ZSM-20 can be suitably prepared by preparing a solution containing sources of an alkali metal oxide, preferably sodium oxide, an oxide of tetraethylammonium, an oxide of aluminum, an oxide of silicon and water and having a composition, in terms of mole ratios of oxides, falling within the following ranges:

|  | Broad | Preferred |
|---|---|---|
| $\dfrac{M^+ - R^+}{M^+}$ | 5-10 | 6-7 |
| $H_2O/SiO_2$ | 10-20 | 12-14 |
| $H_2O/OH^-$ | 15-30 | 19-21 |
| $SiO_2/Al_2O_3$ | 30-32 | 30.5-31.5 | wherein R is a tetraethylammonium cation and M is an alkali metal cation, and maintaining the mixture until crystals of the zeolite are formed. Thereafter, the crystals are separated from the liquid and recovered. Typical reaction conditions consist of heating the foregoing reaction mixture to a temperature of from about 50° C. for a period of time of from about 1 week to about 7 weeks. A more preferred temperature range is from about 90° C. to about 120° C. with the amount of time at a temperature in such range being from about 2 weeks to about 1 month.

The digestion of the gel particles is carried out until crystals form. The solid product is separated from the reaction medium, as by cooling the whole to room temperature, filtering and water washing.

The crystalline product is dried, e.g. at 230° F., for from about 8 to 24 hours. Of course, milder conditions may be employed if desired, e.g. room temperature under vacuum.

The composition for the synthesis of synthetic ZSM-20 can be prepared utilizing materials which can supply the appropriate oxide. Such compositions include aluminates, alumina, silicates, silica hydrosol, silica gel, silica acid and hydroxides.

Crystal size and crystallization time of the ZSM-20 composition will vary with the nature of the reaction mixture employed.

Synthetic ZSM-20, in accordance with the present invention, has the original cation associated therewith replaced by appropriate cations, for example hydrogen, ammonium and cations of the rare earth metals.

Typical ion exchange techniques would include contacting the synthetic ZSM-20 zeolite with a salt of the desired replacing cation or cations. Although a wide variety of salts can be employed, particular preference is given to chlorides, nitrates and sulfates.

Representative ion exchange techniques are disclosed in a wide variety of patents including U.S. Pat. Nos. 3,140,249; 3,140,251; and 3,140,253.

Following contact with the salt solution of the desired replacing cation, the zeolite is then preferably washed with water and dried at a temperature ranging from 150° F. to about 600° F. and thereafter may be calcined in air or other inert gas at temperature ranging from about 500° F. to 1500° F. for periods of time ranging from 1 to 48 hours or more to produce a catalytically active thermal decomposition product thereof.

Regardless of the cations replacing the alkali metal in the synthesized form of the ZSM-20, the spatial arrangement of the aluminum, silicon and oxygen atoms which form the basic crystal lattices of ZSM-20 remains essentially unchanged by the described replacement of alkali metal as determined by taking an X-ray powder diffraction pattern of the ion exchanged material.

For ion exchanging the ZSM-20 zeolite, the contemplated rare earth metals include Sc, Y, La, Ce, Pr, Nd, Pm, Sm, Eu, Gd, To, Dy, Ho, Er, Tm, Yo and Lu.

In carrying out the above ion exchange, the rare earth cations can be provided from the salt of a single metal or preferably a mixture of metals such as rare earth chlorides or didymium chlorides. Such mixtures are usually introduced as a rare earth chloride solution which, as used herein, has reference to a mixture of rare earth chlorides consisting essentially of the chlorides of lanthanum, cerium, praseodymium, and neodymium, with minor amounts of samarium, gadolinium, and yttrium. This solution is commercially available and contains the chlorides of a rare earth metal mixture having the relative composition cerium (as $CeO_2$) 48% by weight, lanthanum (as $La_2O_3$) 24% by weight, praseodymium (as $Pr_6O_{11}$) 5% by weight, neodymium (as $Nd_2O_3$) 17% by weight, samarium (as $Sm_2O_3$) 3% by weight, gadolinium (as $Gd_2O_3$) 2% by weight, yttrium (as $Y_2O_3$) 0.2% by weight, and other rare earth metal oxides 0.8% by weight. Didymium chloride is also a mixture of rare earth metal chlorides, but having a low cerium content. It consists of the following rare earth metals determined as oxides; lanthanum 45–46% by weight; cerium, 1–2% by weight; praseodymium, 9–10% by weight, neodymium, 32–33% by weight; samarium, 5–6% by weight; gadolinium 3–4% by weight; yttrium, 0.4% by weight; other rare earths 1–2% by weight. It is to be understood that other mixtures of rare earths are equally applicable in the instant invention.

The catalyst of the present invention can be further improved by the introduction of other metal cations, such as $Ca^{+2}$, as in the case of Y-zeolite. Exemplary of such metals are titanium, zirconium, aluminum, vanadium, chromium, manganese, iron, cobalt and the like. The chemical properties of the metals, i.e. its atomic radius, degree of ionization and the like will determine its suitability for exchange with the ZSM-20. In addition, certain divalent metal cations such as calcium, magnesium, and barium may be used with ammonium compounds such as ammonium chloride, to provide the necessary acid sites within the ZSM-20 catalyst by conventional exchange techniques; the portion of the acid sites being formed by heating the ZSM-20 to drive off ammonia. It is also to be understood that the catalyst of the present invention may be further steamed and/or sulfided to improve its stability and/or activity.

The ZSM-20 catalyst may be employed directly as a catalyst or it may be combined with a suitable support or binder. The particular chemical composition of the latter is not critical. It is, however, necessary that the support or binder employed be thermally stable under the conditions at which the conversion reaction is carried out. Thus, it is contemplated that solid porous absorbents, carriers and supports of the type heretofore employed in catalytic operations may feasibly be used in combination with the ZSM-20. Such materials may be catalytically inert or may posses an intrinsic catalytic activity or an activity attributable to close association or reaction with the ZSM-20. Such materials include by way of examples, dried inorganic oxide gels and gelatinous precipitates of alumina, silica, zirconia, magnesia, thoria, titania, boria and combinations of these oxides with one another and with other components. Other suitable supports include activated charcoal, mullite, kieselguhr, bauxite, silicon carbide, sintered alumina and various clays.

The ZSM-20 may be intimately composited with a suitable binder, such as inorganic oxide hydrogel or clay, for example, by ball milling the two materials together over an extended period of time, preferably in the presence of water, under conditions to reduce the particle size of the ZSM-20 to a weight mean particle diameter of less than 40 microns and preferably less than 15 microns. Also, the ZSM-20 may be combined with and distributed throughout a gel matrix by dispersing the ZSM-20 in powdered form in an inorganic oxide hydrosol. In accordance with this procedure, the finely divided ZSM-20 may be dispersed in an already prepared hydrosol or, as is preferred, where the hydrosol is characterized by a short time of gelation, the finely divided ZSM-20 may be added to one or more of the reactants used in forming the hydrosol or may be admixed in the form of a separate stream with streams of the hydrosol-forming reactants in a mixing nozzle or other means where the reactants are brought into intimate contact. The powder-containing inorganic oxide hydrosol sets to a hydrogel after lapse of a suitable period of time and the resulting hydrogel may thereafter, if desired, be exchanged to introduce selected ions into the ZSM-20 and then dried and calcined.

The inorganic oxide gel employed, as described above as a matrix for the ZSM-20 may be a gel of any hydrous inorganic oxide, such as, for example, aluminous or siliceous gels. While alumina gel or silica gel may be utilized as a suitable matrix, it is preferred that the inorganic oxide gel employed be a cogel of silica and an oxide of at least one metal selected from the group consisting of metals of Groups II-A, IIB, and IV-A of the Periodic Table. Such components include, for example, silica-alumina, silica-magnesia, silica-zirconia, silica-thoria, silica-beryllia, silica-titania as well as ternary combinations such as silica-alumina-thoria, silica-alumina-zirconia, silica-alumina-magnesia and silica-magnesia-zirconia. In the foregoing gels, silica is generally present as the major component and the other oxides of metals are present in minor proportion. Thus, the silica content of such gels is generally within the approximate range of 55 to 100 weight percent with the metal oxide content ranging from zero to 45 weight percent. The inorganic oxide hydrogels utilized herein and hydrogels obtained therefrom may be prepared by any method well known in the art, such as, for example, hydrolysis of ethyl ortho-silicate, acidification of an alkali metal silicate and a salt of a metal, the oxide of which it is desired to cogel with silica, etc. The relative proportions of finely divided ZSM-20 and inorganic oxide gel matrix may vary widely with the ZSM-20 content ranging from about 2 to about 90 percent by weight and more usually, particularly where the composite is prepared in the form of beads, in the range of about 5 to about 50 percent by weight of the composite. It will be appreciated that base exchange of the metal, ammonium, or hydrogen cations to produce the necessary acid sites within the ZSM-20 may be carried out either before or after the ZSM-20 has been incorporated into the matrix binder material.

The catalyst of ZSM-20 employed in the process of this invention may be used in the form of small fragments of a size best suited for operation under the specific conditions existing. Thus, the catalyst may be in the form of a finely divided powder or may be in the form of pellets of 1/16" to ⅛" size, for example, obtained upon pelleting the ZSM-20 with a suitable binder such as clay.

The operating temperature of the described alkylation process may extend from room temperature to 400° F.; preferably the process is conducted at temperatures from 150° to 250° F.

The pressures employed in the present process may extend over a considerable range, i.e. from about atmospheric to about 1500 psig. Preferably the pressure is sufficient to maintain at least one of the reactants or reaction products in a liquid phase. Liquid phase operation is believed to promote the length of catalyst activity by preventing the formation of olefinic polymerization and by washing out other by-product high molecular weight compounds from the internal structure of the catalyst caused by the above-mentioned side reactions. In addition, liquid phase operation promotes greater catalytic activity by increasing the residence time of the reactants within the catalyst structure. Liquid phase operation is considered particularly desirable for alkylation reactions in which the unsteamed, highly active catalysts are employed. Apparently such operation permits these catalysts to exhibit greater selective activity for alkylation without promoting undesirable side reactions such as polymerization of the olefins which may occur during vapor phase operation.

The amount of catalyst used in the present process may be varied over relatively wide limits. In general, the amount of catalyst as measured by weight hourly space velocity of the olefin may be from about 0.1 to 10. It will be realized that the amount of catalyst selected for a particular reaction will be determined by several variables including the reactants involved as well as the nature of the catalyst and the operating conditions to be used.

In accordance with the process of this invention, the relative molar ratio between the isoparaffin reactant and the olefin alkylating agent is in the range of 3:1 to 20:1, preferably 5:1 to 15:1 and 9:1 is particularly preferred.

The olefin alkylating agent may desirably in some instances be employed in a fluid media which contains a major proportion of an inert diluent. The advantages of such operation will be readily apparent because of the availability and low cost of obtaining such diluent process treatment during hydrocarbon processing. It will further be appreciated that the particular operating conditions employed in the present process will depend on the specific alkylation reaction being effected. Such conditions as temperature, pressure, space velocity and molar ratio of the reactants will have important effects on the overall process. Also the operating conditions for the alkylation reaction in accordance with the process of this invention may be varied so that the same may be conducted in gaseous phase, liquid phase, or mixed liquid-vapor phase, depending upon product distribution, degree of alkylation, as well as the pressures and temperatures at which the alkylation is effected.

The following examples will serve to illustrate the process of the invention without limiting the same.

EXAMPLE 1

A rare earth metal hydrogen Y zeolite (REHY) catalyst is prepared for comparison purposes from sodium Y type zeolite by exchange with a commercial mixture of rare earth metal chlorides. After drying at 250° F. (120° C.) for 16 hours, it is calcined at 1000° F. (537° C.) for 3 hours in a stream of dry air. The zeolite is further exchanged with ammonium chloride, dried and activated. The catalyst composition is shown in Table 2.

EXAMPLE 2

NaZSM-20 (according to Example 1 of U.S. Pat. No. 3,972,983) was prepared from a solution comprising 14.1 grams sodium aluminate (43.5 $Al_2O_3$, 30.2 $Na_2O$ and 24.9% $H_2O$), 764 ml. of 1.51 normal solution of tetraethylammonium hydroxide (prepared from tetraethylammonium bromide) and 6.0 grams of 50 percent NaOH were mixed in a 1 gallon Waring Blender for 1–2 minutes. A 282 gram quantity of tetramethylorthosilicate was then added to the above mixture gradually within about 15 minutes. After addition of the silicate ester was completed, the mixture was stirred for 30 minutes to hydrolyze the ester completely. The slurry formed at this point in time was allowed to stand at room temperature for 3 days, and then placed in a 100° C. steam chest. Crystallization at 100° C. took about 4 weeks. The product crystals were filtered out of solution and water washed until the pH of the wash water was about 8.

Chemical analysis of the crystalline product led to the following compositional figures:

| Composition | Wt % | Mole Ratio on $Al_2O_3$ Basis |
|---|---|---|
| N | 1.61 | — |
| Na | 3.3 | — |
| $Al_2O_3$ | 15.1 | 1.0 |
| $SiO_2$ | 78.1 | 8.8 |
| $N_2O$ | — | 0.592 |
| $Na_2O$ | — | 0.486 |

EXAMPLE 3

A HZSM-20 catalyst is prepared from NaZSM-20 by precalcining the NaZSM-20 in nitrogen and exchanging the same with ammonium chloride. After drying, the product is air calcined to activate the same. The catalyst composition is shown in Table 2.

EXAMPLE 4

A rare earth HZSM-20 is prepared from NaZSM-20 by precalcining the same in nitrogen followed by exchanging with a commercial rare earth metal chloride mixture. The product is dried at 250° F., (120° C.), calcined in air at 1000° F. (537° C.), further exchanged with an ammonium chloride solution, dried at 250° F. (120° C.) and air calcined at 1000° F. (537° C.) for 3 hours. The catalyst composition is shown in Table 2.

TABLE 2

| Catalyst wt % (Ignited Basis) | Catalyst Composition | | |
|---|---|---|---|
| | REHY | HZSM-20 | REZSM-20 |
| $Na_2O$ | 0.2 | 1.2 | 0.03 |
| $RE_2O_3$ | 14.7 | — | 10.0 |
| $Al_2O_3$ | 19.5 | 15.7 | 15.7 |
| $SiO_2$ | 60.1 | 79.7 | 79.7 |
| Molar Ratio | | | |
| $RE_2O_3/Al_2O_3$ | 0.24 | — | 0.20 |
| $SiO_2/Al_2O_3$ | 5.2 | 8.6 | 8.6 |

EXAMPLE 5

Each of the catalyst of Examples 1, 3 and 4 were employed to effect the alkylation of isobutane with 1-butene. All the alkylation runs were performed in a 316 stainless steel batch, 300 ml stirred autoclave under sufficient $N_2$ pressure to maintain a liquid phase. C.P. grade isobutane and 1-butene were used. The isobutane to butene molar ratio was 9:1. The total amount of isobutane was, as measure by a typical Jerguson gauge, charged into the autoclave and then 1-butene was added slowly by a pump at the rate of 40 cc/hour until the specified amount was reached. The reactor was then sealed and reacted for a total of 4 hours. The reaction temperature was about 195° F. (90° C.). Material balance was done by collecting the whole product in an acetone-dry ice cold trap. The collected product was weighed and then weathered in room temperature through a gas meter to measure the gas volume. The weathered gas was collected in a gas bag and sampled for Chromatographic analysis. The weathered liquid product was reweighed and sampled for G.C. analysis. The amount of olefin reacted was determined from the amount of olefin charged and that remaining in the weathered products. Detailed results are shown in Table 3. It will be noted that the yield of $C_5+$ liquid product per gram of 1-butene converted, was 14% higher for the REHZSM-20 than for the REHY. While the product distribution of $C_5$–$C_9$ was similar for the two catalysts, the REHZSM-20 produced about 22% more trimethylpentanes and 18% less undesired dimethylhexanes and methylheptanes than the REHY catalyst. The estimated research octane number is higher for the REHZSM-20 (84 vs 78).

TABLE 3

| Catalyst | Isobutane-1-butene alkylation | | |
|---|---|---|---|
|  | REHY | HZSM-20 | REHZSM-20 |
| Temp. °F. (°C.) | 193 (89) | 195 (90) | 195 (90) |
| Pressure, psig (atm) | 335 (22.8) | 350 (23.8) | 350 (23.8) |
| WHSV (1-$C_4$=) | 7.21 | 7.21 | 7.21 |
| $iC_4$/1-$C_4$= (Molar) | 9 | 9 | 9 |
| Yield, $C_5+/C_4$= |  |  |  |
| Conv. | 1.02 | 1.00 | 1.18 |
| 1-$C_4$= Conversion, wt % | 44 | 41 | 57 |
| Material Balance, wt % | 101.7 | 105.5 | 106.5 |
| RON (estimated) | 78 | 82 | 84 |
| $C_5+$ Prod. Distr. wt % |  |  |  |
| $C_5$ | 3.8 | 4.2 | 2.5 |
| $C_6$ | 6.6 | 7.3 | 4.8 |
| $C_7$ | 7.9 | 10.0 | 7.6 |
| $C_8$ | 79.0 | 74.2 | 81.5 |
| $C_9+$ | 2.7 | 4.3 | 3.6 |
| $C_8$ Prod. Distr. % |  |  |  |
| Trimethylpentanes | 54.2 | 62.4 | 66.4 |
| Dimethylhexanes | 33.6 | 28.5 | 24.6 |
| Methylheptanes | 11.9 | 8.9 | 8.8 |
| Trimethylpentanes, Distr. % |  |  |  |
| 2,2,4 | 18.2 | 28.2 | 23.7 |
| 2,2,3 | 9.0 | 9.9 | 7.4 |
| 2,3,4 | 38.9 | 31.4 | 36.1 |
| 2,3,3 | 33.9 | 30.5 | 32.7 |

EXAMPLES 6–9

Employing the process conditions of Example 5 and using the catalyst of Example 3 effective alkylation is accomplished employing (Example 6) isobutane and 1-butene; (Example 7) isopentane and propylene; (Example 8) ethylisobutane and ethylene; and (Example 9) dimethylisopentane and ethylene each in a molar ratio of the isoparaffin to olefin of about 5:1.

EXAMPLES 10–13

Employing the process conditions of Example 5 and using the catalyst of Example 4, effective alkylation is accomplished employing (Example 10) isobutane and 1-hexene; (Example 11) isopentane and 1-pentene; (Example 12) isobutane and 1-heptene; and (Example 13) isopentane and propylene; each in a molar ratio of the isoparaffin to olefin of about 15:1.

What is claimed is:

1. A process for effecting alkylation of isoparaffins which comprises contacting an isoparaffin containing from 4 to 7 carbon atoms with an olefin containing from 2 to 7 carbon atoms at a temperature of from about room temperature to about 400° F., a pressure sufficient to maintain at least the isoparaffin or olefin or both in the liquid phase and a molar ratio of isoparaffin to olefin of from about 3:1 to about 20:1 in the presence of a catalyst comprising a synthetic crystalline zeolite exhibiting an X-ray powder diffraction pattern which shows the significant lines set forth in Table 1.

2. The process of claim 1 wherein said isoparaffin contains 4 carbon atoms and said olefin contains from 2 to 4 carbon atoms.

3. The process of claim 2 wherein said isoparaffin is isobutane and said olefin is 1-butene.

4. The process of claim 1 wherein said temperature is from about 150° F. to about 250° F.

5. The process of claim 1 wherein said pressure is from about atmospheric to about 1500 psig.

6. The process of claim 1 wherein said molar ratio of isoparaffin to olefin is from about 5:1 to about 15:1.

7. The process of claim 1 wherein said zeolite has been subjected to ion exchange with cations selected from the group consisting of hydrogen, hydrogen precursors, yttrium, rare earth metals and combinations thereof.

8. The process of claim 7 wherein said cations are hydrogen.

9. The process of claim 7 wherein said cations are rare earth metals.

10. The process of claim 7 wherein said cations are hydrogen and rare earth metals.

11. The process of claim 7 wherein said zeolite has been further subjected to ion exchange with cations selected from the group consisting of titanium, zirconium, aluminum, vanadium, chromium, manganese, iron, cobalt, calcium, magnesium, barium and combinations thereof.

12. The process of claim 7 wherein said zeolite has been thermally treated at a temperature of from 500° F. to 1500° F. subsequent to said ion exchange.

13. The process of claim 7 wherein said rare earth metals are selected from the group consisting lanthanum, cerium, praseodymium, neodymium, samarium, gadolinium and combinations thereof.

14. The process of claim 1 wherein said catalyst further comprises a binder material.

15. The process of claim 14 wherein said binder material is selected from the group consisting of an inorganic oxide, clay and a combination thereof.

* * * * *